(12) United States Patent
Stoianovici et al.

(10) Patent No.: US 10,751,034 B2
(45) Date of Patent: Aug. 25, 2020

(54) GEOMETRIC BIOPSY PLAN OPTIMIZATION

(71) Applicant: THE JOHNS HOPKINS UNIVERSITY, Baltimore, MD (US)

(72) Inventors: Dan Stoianovici, Reisterstown, MD (US); Doyoung Chang, Rosedale, MD (US); Misop Han, West Friendship, MD (US)

(73) Assignee: The Johna Hopkins University, Baltimore, MD (US)

( * ) Notice: Subject to any disclaimer, the term of this patent is extended or adjusted under 35 U.S.C. 154(b) by 392 days.

(21) Appl. No.: 15/785,825

(22) Filed: Oct. 17, 2017

(65) Prior Publication Data
US 2018/0103938 A1    Apr. 19, 2018

Related U.S. Application Data

(60) Provisional application No. 62/409,040, filed on Oct. 17, 2016.

(51) Int. Cl.
*A61B 5/00* (2006.01)
*A61B 10/02* (2006.01)
(Continued)

(52) U.S. Cl.
CPC ........ *A61B 10/0241* (2013.01); *A61B 5/4381* (2013.01); *A61B 5/7275* (2013.01);
(Continued)

(58) Field of Classification Search
CPC ... A61B 10/0241; A61B 34/10; A61B 5/4381; A61B 5/7275; A61B 2034/105;
(Continued)

(56) References Cited

U.S. PATENT DOCUMENTS

| 5,267,328 A | 11/1993 | Gouge |
| 2007/0293787 A1 | 12/2007 | James et al. |

(Continued)

FOREIGN PATENT DOCUMENTS

| WO | 2007137179 A2 | 11/2007 |
| WO | 2013049845 A2 | 4/2013 |

OTHER PUBLICATIONS

Zeng, et al., Probability of cancer detection with optimized prostate biopsy protocols. Proceedings of SPIE—The International Society for Optical Engineering. 2001. 4319.

(Continued)

*Primary Examiner* — Max F Hindenburg
(74) *Attorney, Agent, or Firm* — Johns Hopkins Technology Ventures

(57) ABSTRACT

The present invention is directed to a method for calculating tumor detection probability of a biopsy plan and for generating a 3D biopsy plan that maximizes tumor detection probability. A capsule shaped volume is modeled to represent the volume that a biopsy core may sample. An optimization method is used to generate a 3D biopsy plan that maximizes probability of tumor detection for predefined biopsy core numbers and length. Risk of detecting insignificant tumors, also determined by size, and probability of a false negative result is automatically calculated. The present invention also includes a method to determine number and length of biopsy cores required for individual patients determined by the balance of the insignificant/significant probability of detection, prostate size and shape, based upon the previously explained 3D biopsy plan generation method.

20 Claims, 12 Drawing Sheets

(51) Int. Cl.
    A61B 34/10      (2016.01)
    G16H 40/63     (2018.01)
    G16H 50/50     (2018.01)
(52) U.S. Cl.
    CPC .............. *A61B 34/10* (2016.02); *G16H 40/63* (2018.01); *G16H 50/50* (2018.01); *A61B 5/4887* (2013.01); *A61B 2034/105* (2016.02); *A61B 2034/107* (2016.02); *A61B 2576/02* (2013.01)
(58) Field of Classification Search
    CPC ............ A61B 2034/107; A61B 5/4887; A61B 2576/02; G16H 50/50; G16H 40/63
    See application file for complete search history.

(56) References Cited

U.S. PATENT DOCUMENTS

| 2009/0093715 | A1* | 4/2009 | Downey | A61B 8/0833 |
|---|---|---|---|---|
| | | | | 600/437 |
| 2012/0087557 | A1 | 4/2012 | Miller et al. | |

OTHER PUBLICATIONS

Ahmed, et al., 2012. A biomedical engineering approach to mitigate the errors of prostate biopsy. Nat Rev Urol 9, 227-231.
Ashley, et al., 2008. Reassessing the Diagnostic Yield of Saturation Biopsy of the Prostate. 53, 976-981.
Babaian, et al., 2000. A comparative analysis of sextant and an extended 11-core multisite directed biopsy strategy. J Urol 163, 152-157.
Bax, et al., 2008. Mechanically assisted 3D ultrasound guided prostate biopsy system. Med Phys 35, 5397-5410.
Bjurlin, et al., 2013. Optimization of Initial Prostate Biopsy in Clinical Practice: Sampling, Labeling and Specimen Processing. J Urol 189 2039-2046.
Chang, et al., 1998. Prospective evaluation of lateral biopsies of the peripheral zone for prostate cancer detection. J Urol 160, 2111-2114.
Chen, et al., 1997. Optimization of prostate biopsy strategy using computer based analysis. J Urol 158, 2168-2175.
Stoianovici, et al., 2014. MRI-Safe Robot for Endorectal Prostate Biopsy. IEEE/ASME Transactions on Mechatronics 19(4), 1289-1299.
Dietrick, et al., 1995. Core cancer length in ultrasound-guided systematic sextant biopsies: a preoperative evaluation of prostate cancer volume. Urology 45, 987-992.
Epstein, et al., 1994. Pathologic and clinical findings to predict tumor extent of nonpalpable (stage T1c) prostate cancer. JAMA 271, 368-374.
Eskew, et al., 1997. Systematic 5 region prostate biopsy is superior to sextant method for diagnosing carcinoma of the prostate. J Urol 157, 199-203.
Eskicorapci, et al., 2005. Individualization of the biopsy protocol according to the prostate gland volume for prostate cancer detection. J Urol 173, 1536-1540.
Giannarini, et al., 2009. Saturation Biopsy of the Prostate: Why Saturation Does Not Saturate. European Association of Urology 56, 619-621.
Han, et al., 2012. Geometric Evaluation of Systematic Transrectal Ultrasound-Guided Prostate Biopsy. J Urol 188.
Ho, et al., 2009. Robotic ultrasound-guided prostate intervention device: system description and results from phantom studies. Int J Med Robot 5, 51-58.
Hooke, et al.,1961. "Direct Search" Solution of Numerical and Statistical Problems. Journal of the ACM 8, 212-229.
Hu, et al., 2012. A biopsy simulation study to assess the accuracy of several transrectal ultrasonography (TRUS)-biopsy strategies compared with template prostate mapping biopsies in patients who have undergone radical prostatectomy. BJU Int 110, 812-820.

Hugosson, et al., 2010. Mortality results from the Göteborg randomised population-based prostate-cancer screening trial. Lancet Oncol 11, 725-732.
Kanao, et al., 2013 Can transrectal needle biopsy be optimised to detect nearly all prostate cancer with a volume of ≥0.5 mL? A three-dimensional analysis. BJU Int 112, 898-904.
Karakiewicz, et al., 1997. Outcome of sextant biopsy according to gland volume. Urology 49, 55-59.
Karakiewicz, et al., 1998. Three-dimensional computer-assisted analysis of sector biopsy of the prostate. Urology 52, 208-212.
Kelloff, et al., 2009. Challenges in clinical prostate cancer: role of imaging. AJR Am J Roentgenol 192, 1455-1470.
Kepner, et al., 2010. Transperineal prostate biopsy: analysis of a uniform core sampling pattern that yields data on tumor volume limits in negative biopsies. Theor Biol Med Model 17, 7-23.
Kiknavelidze, et al., 2006. Prostate cancer detection rate in patients with obstructive voiding symptoms by sextant biopsy preliminary results. Georgian Med News 133, 9-14.
Kim, et al., 2013. Ultrasound Probe and Needle guide calibration of robotic US scanning and targeting. IEEE Transactions on Biomedical Engineering vol. 60.
Kommu, 2005 Re: Individualization of the biopsy protocol according to the prostate gland volume for prostate cancer detection. J Urol 174, 2068.
Leissner, et al., 1979. The Weight of the Human Prostate. Scandinavian J of Urology 13, 137-142.
Loeb, et al., 2013. Systematic review of complications of prostate biopsy. Eur Urology 64, 876-892.
Han, et al., 2011. Tandem-robot Assisted Laparoscopic Radical Prostatectomy to Improve the Neurovascular Bundle Visualization: A Feasibility Study. Urology 77(2), 502-506.
McNeal, et al., 1988. Zonal distribution of prostatic adenocarcinoma. Correlation with histologic pattern and direction of spread. Am J Surg Pathol 12, 897-906.
Miyake, et al., 2007 Additional sampling of dorsal apex on systematic prostate biopsy: impact on early detection of prostate cancer. Urology 69, 738-742.
Mohan, et al., 2007. A 3D computer simulation to study the efficacy of transperineal versus transrectal biopsy of the prostate. Int. J. Computer Assisted Radiology and Surgery 1, 351-360.
Moussa, et al., 2010 Importance of additional "extreme" anterior apical needle biopsies in the initial detection of prostate cancer. Urology 75, 1034-1039.
Mozer, et al., 2009. Mapping of transrectal ultrasonographic prostate biopsies: quality control and learning curve assessment by image processing. J Ultrasound Med 28, 455-460.
Muntener, et al., 2008. Transperineal prostate intervention: robot for fully automated MR imaging-system description and proof of principle in a canine model. Radiology 247, 543-549.
Natarajan, et al., 2011. Clinical application of a 3D ultrasound-guided prostate biopsy system. Urol Oncol 29, 334-342.
Naughton, et al., 2000. A prospective randomized trial comparing 6 versus 12 prostate biopsy cores: Impact on cancer detection. J Urol 164, 388-392.
Ou, et al., 2009. Sampling the spatial patterns of cancer: optimized biopsy procedures for estimating prostate cancer volume and Gleason Score. Med Image Anal 13, 609-620.
Presti, et al., 2000. The optimal systematic prostate biopsy scheme should include 8 rather than 6 biopsies: Results of a prospective clinical trial. J Urol 163, 163-167.
Rabbani, et al., 1998. [Incidence and clinical significance of false-negative sextant biopsies of the prostate]. Urologe A 37, 660.
Scattoni, et al., 2010. Biopsy schemes with the fewest cores for detecting 95% of the prostate cancers detected by a 24-core biopsy. European Urology 57, 1-8.
Schroder, et al., 2009. Screening and Prostate-Cancer Mortality in a Randomized European Study. N Engl J Med 360, 1320-1328.
Shen, et al., 2004. Optimized prostate biopsy via a statistical atlas of cancer spatial distribution. Med Image Anal 8, 139-150.
Siegel, et al., 2014. Cancer statistics, 2014. CA Cancer J Clin 64, 9-29.

(56) References Cited

OTHER PUBLICATIONS

Singh, et al., 2004 Six additional systematic lateral cores enhance sextant biopsy prediction of pathological features at radical prostatectomy. J Urol 171, 204-209.
Sofer, et al., 2003. Optimal Biopsy Protocols for Prostate Cancer. Annals of Operations Research 119, 63-74.
Spitzer, et al., 1996. The visible human male: a technical report. J Am Med Inform Assoc 3, 118-130.
Srimathveeravalli, et al., 2014. MRI-Safe Robot for Targeted Transrectal Prostate Biopsy: Animal Experiments. British Journal of Urology International 113, 977-985.
Stoianovici, et al., 2013. Endocavity Ultrasound Probe Manipulators. IEEE ASME Trans Mechatron. Jun. 2013; 18(3): 914-921.
Stoianovici, et al., 2007. "MRI Stealth" robot for prostate interventions. Minim Invasive Ther Allied Technol 16, 241-248.
Terris, 1999. Sensitivity and specificity of sextant biopsies in the detection of prostate cancer: preliminary report. Urology 54, 486-489.
Torczon, 1997. On the Convergence of Pattern Search Algorithms. SIAM J. Optim 7, 1-25.
Uzzo, et al., 1995. The influence of prostate size on cancer detection. Urology 46, 831-836.
Welch, et al., 2007. Detection of prostate cancer via biopsy in the Medicare-SEER population during the PSA era. J Natl Cancer Inst 99, 1395-1400.
Xu, et al., 2008. Real-time MRI-TRUS fusion for guidance of targeted prostate biopsies. Comput Aided Surg 13, 255-264.
Hodge, et al., 1989. Random systematic versus directed ultrasound guided transrectal core biopsies of the prostate. J Urol 142, 74-75.
Geoffrion, et al., 1972. Generalized Bender's decomposition. J Optim Theory and its Appl 10, 237-253.
Lin, et al., 1988. Dynamic elastic interpolation for 3D medical inage reconstruction from serial cross section. IEEE Trans Med Imaging 7, 225-232.
Xuan, et al., 1997. Surface Reconstruction and Visualization of the surgical prostate model. Proceedings of the SPIE Medical Imaging Conference 3031, 50-61.
Zeng et al., 2000. Building an accurate 3D map of prostate cancer using computerized models of 280 whole-mounted radical prostatectomy specimens. Proceedings of the SPIE Medical Imaging Conference 3976, 466-477.
Abeyratne, et al., Higher-Order Vs. Second Order Statistics in Ultrasound Image Deconvolution, IEEE Transactions on Ultrasonics, Ferroelectrics, and Frequency Control , Nov. 1997.
Bauer, et al., 3-D Computer simulated prostate models: Lateral prostate biopsies increase the detection rate of prostate cancer. Urology, 53(5):961-967, 1999.
Feleppa, et al., Typing of prostate tissue by ultrasonic spectrum analysis, IEEE Transactions on Ultrasonics, Ferroelectrics, and Frequency Control, 43:609-619, 1996.
Daneshgari, et al., Computer simulation of the probability of detecting low volume carcinoma of the prostate with six random systematic core biopsies. Urology, 45: 604-609, 1995.
Flanigan, et al., Accuracy of digital rectal examination and transrectal ultrasonography in localizing prostate cancer. J. Urol., 152: 1506, 1994.
Giesen, et al., Computer analysis of transrectal ultrasound images of the prostate for the detection of carcinoma: A prospective study in radical prostatectomy specimens. J. Urology 154: 1397-1400, 1995.
Goto, et al., Distinguishing clinically important from unimportant prostate cancers before treatment: value of systematic biopsies. J. Urol., 156: 1059-1063, 1996.
Jain, et al., 2000. Filterbank-based fingerprint matching. IEEE Trans Image Proc 9, 846-859.
Knoll, et al., 1999, Outlining of the prostate using snakes with shape restrictions based on the wavelet transform. Pattern Recognition 32, 1767-1781.
Nelson, et al., 1997. Interactive acquisition, analysis, and visualization of sonographic volume data. Imaging Systems and Technology 8, 26-37.
Pathak, et al., 1998. Quantitative three-dimensional transrectal ultrasound (TRUS) for prostate imaging. Proc SPIE.
Stamey, Making the most out of six systematic sextant biopsies. Urology. Jan. 1995;45(1):2-12.
Zeng, et al., 1998. Optimizing prostate needle biopsy through 3D simulation. Proc SPI.

* cited by examiner

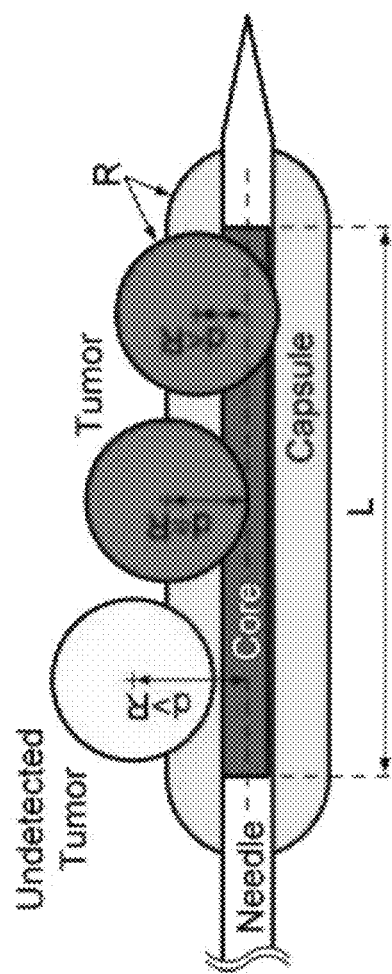
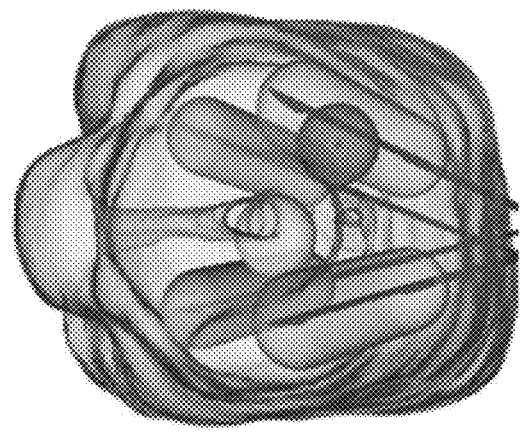
FIG. 3A
FIG. 3B

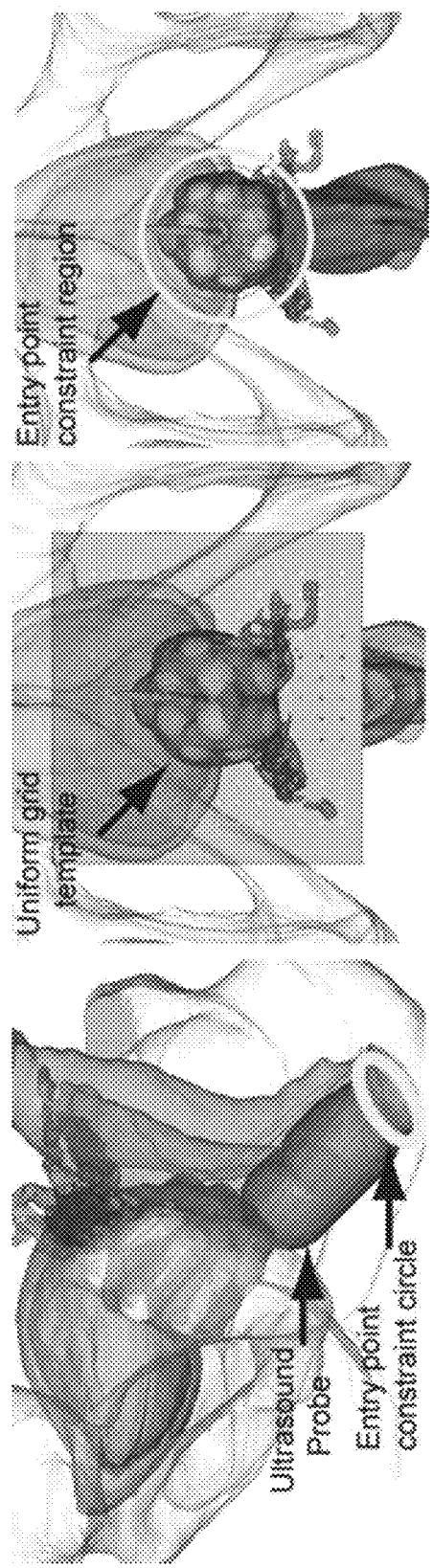

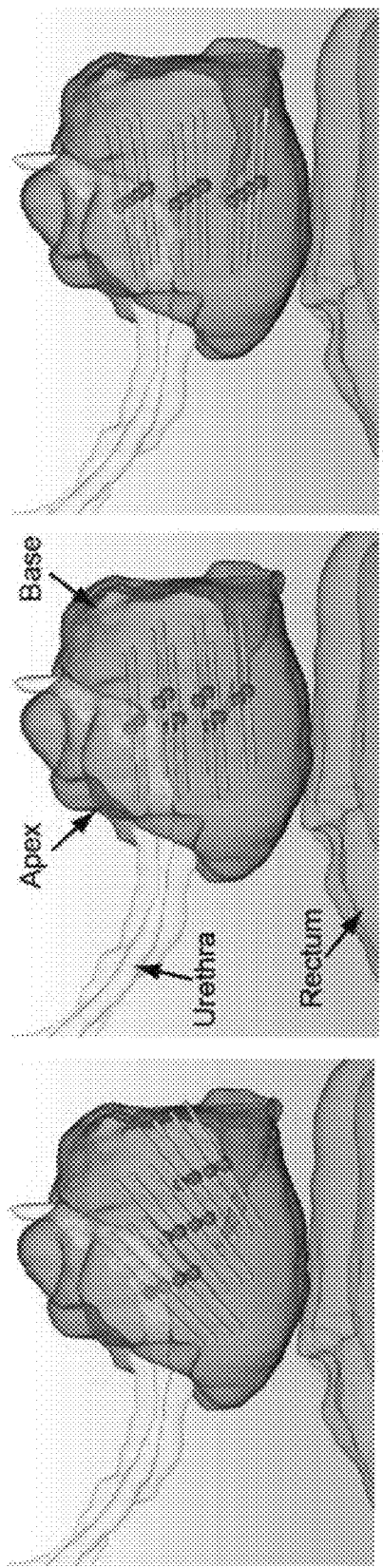

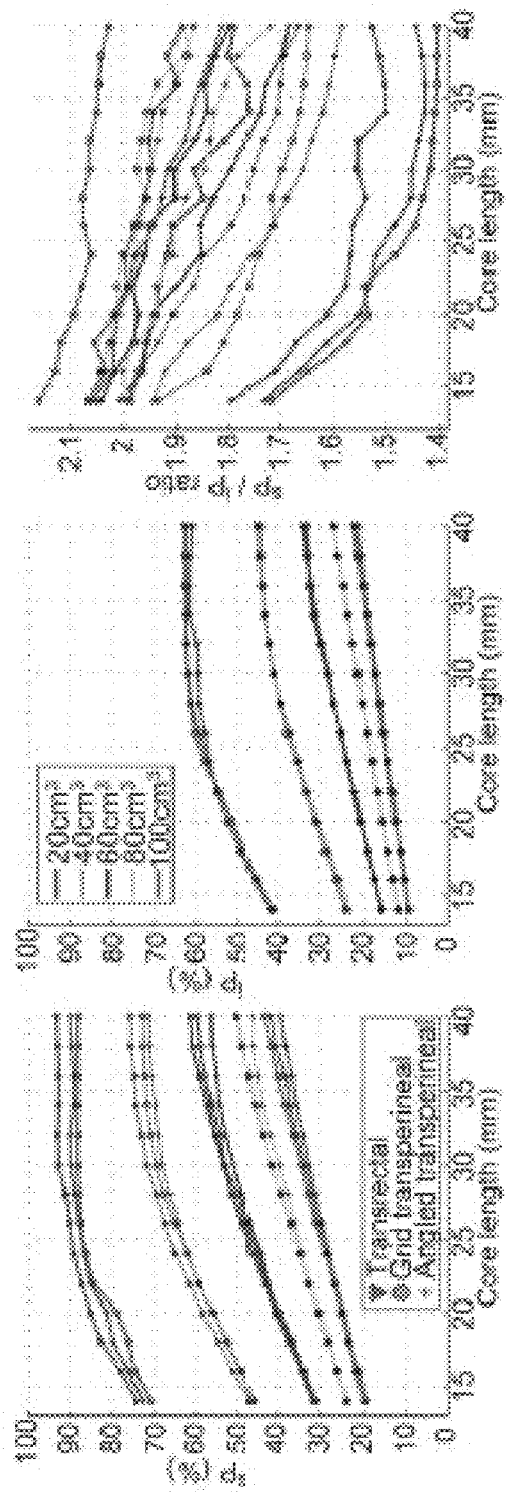

GEOMETRIC BIOPSY PLAN OPTIMIZATION

CROSS REFERENCE TO RELATED APPLICATIONS

This application claims the benefit of U.S. Provisional Patent Application No. 62/409,040, filed on Oct. 17, 2016, which is incorporated by reference herein, in its entirety.

FIELD OF THE INVENTION

The present invention relates generally to biopsy. More particularly the present invention relates to a method for geometric biopsy plan optimization.

BACKGROUND OF THE INVENTION

In 2014, an estimated 233,000 new cases of prostate cancer (PCa) were diagnosed in the US alone. Studies have shown that it is necessary to treat many men to prevent one death from PCa and that significant overtreatment exists. Even so, PCa caused an estimated 29,480 mortalities in 2014 alone. This data underscores the need for more specific PCa screening tests and more reliable PCa diagnosis at biopsy.

Systematic, untargeted prostate biopsy is the current gold standard for PCa diagnosis. Ideally, the goal is to uniformly distribute the biopsy cores according to an extended sextant biopsy plan. But a coordinate based geometric definition of the biopsy plan is typically unavailable. Rather, current biopsy plans are simplistically represented by a two dimensional (2D) cross-section of the gland showing a grid of points. This leaves room for subjective interpretation. Moreover, the number and length of the biopsy cores are not typically optimized for individual patients.

The most common way of diagnosing PCa is the transrectal ultrasound (TRUS) guided prostate biopsy. More than 1 million procedures are performed each year in the United States and Europe. While targeted biopsy methods (currently using ultrasound to magnetic resonance imaging (MRI) fusion) are being investigated for high risk patients, the most numerous, primary biopsies are still performed based on TRUS guided systematic extended sextant biopsy plans that are supposed to sample the gland uniformly. However, clinical data shows that systematic biopsies have low sensitivity and low negative predictive value. Studies have confirmed that biopsy samples are often clustered and miss regions, leading to both over- and under-sampled regions of the prostate, which increase the likelihood of detecting insignificant cancer and obtaining false negative biopsy results. Among other factors such as manual execution errors, biopsy planning is a major cause of unreliable prostate biopsy localization.

The current systematic extended sextant plans are poorly defined from a geometric standpoint. The typical 12-core extended sextant biopsy is to uniformly sample at Left/Right×Medial/Lateral×Apex/Mid/Base of the prostate. The current representation of the plan is a schematic of a grid of points on a 2D coronal section of the prostate. The basic and extended sextant plans, for example, are shown in FIG. 1A and FIG. 1B. This definition is vague, lacking the coordinate location of the cores and leaving much room for subjective interpretation. In 3D the uncertainty widens, as exemplified in FIG. 1C. It is unclear where the plane of grid should be, or whether the cores should be coplanar.

An optimal biopsy plan should be defined by 1) the number of cores and 2) core coordinate locations and directions. Several studies have been conducted to compare different number of cores (e.g. 6, 8, 12, 14, 20 cores), locations (e.g. additional cores in the apex), and directions (e.g. more lateral). Meanwhile, the American Urological Association (AUA) has recommended to use the 12-core extended sextant plan with apical and far-lateral locations of the gland, based on a literature review of clinical results.

However, other authors have reported mixed results, for example different detection rates for the same number of cores and higher detection rate with fewer cores. Possible reasons of this inconsistency may be due to patient selection differences in core placement between urologists for the same biopsy plan, and low repeatability of biopsy even for the same urologist. Moreover, false-negative biopsy rates could not be evaluated in these studies since the reference tests were based on radical prostatectomy specimens, suggesting that the true PCa detection rate could be even lower.

Biopsy plans are not typically customized for individual patients. The only parameter that may sometimes change the biopsy plans is the prostate volume. Yet it remains unclear if and how the biopsy plan should be adjusted for different prostate volume and the 12-core plan remains commonly used regardless of the volume. It was, however, suggested that since there is large variation in prostate volumes (from 10 $cm^3$ to hundreds of $cm^3$) biopsy core numbers need to be adjusted accordingly. Yet, other clinical studies found that there is no advantage on increasing the number of cores for larger prostates, leaving the debate still open.

Computer simulated biopsy studies have been performed based on statistical atlases using whole mount prostates. In these studies, the detection rates of different biopsy plans were measured by calculating the number of tumors detected by the simulated biopsy cores, and the number of tumors missed in each case. These groups have been first to propose and implement analytical prostate biopsy optimizations by precisely calculating the number of cores needed to achieve a certain detection rate. Among them, results were somewhat different possibly due to different statistical maps of tumor occurrence used by each group, or different placement of the cores for the same biopsy plan. Because the methods were used on the resected gland, they could not consider the path of needle insertion.

Other previous approaches used 2D analyses to determine the probability of significant cancer detection for transperineal biopsy using a grid template of equally spaced holes. This probability is calculated based on the area covered by the cores per unit grid on the transversal 2D cross section. The study demonstrated the ability to precisely calculate the probability based on prostate geometry and was able to predict the probability of a false negative result for an individual patient.

It would therefore be advantageous to provide a method that improves tumor detection probability of a given biopsy plan.

SUMMARY

According to a first aspect of the present invention a method of calculating tumor detection probability of a biopsy plan including calculating insignificant tumor detection probability. The method includes generating a three-dimensional biopsy plan that increases the probability of the insignificant tumor detection probability. Additionally, the method includes calculating probability of a false negative detection of tumor using the three-dimensional biopsy plan, and determining a number and length of biopsy cores required to execute the three-dimensional biopsy plan.

In accordance with an aspect of the present invention, the method includes implementing the method using a non-transitory computer readable medium. The method also includes calculating tumor detection probability with steps such as, setting a bounding box for a tumor detection area and a voxel size to discretize this volume at a predetermined level of resolution; iterating through all voxels; checking if a voxel center is within the tumor detection area, and if so add it to a set $\Gamma$; iterating through all voxels of set $\Gamma$; verifying if the voxel center falls within any of the biopsy cores of a set $\Pi$; counting the voxel with a center that falls within any of the biopsy cores of set $\Pi$ as sampled by adding it to a set $\Omega$; and calculating tumor prediction probability as the ratio of the number of elements of the $\Omega$ and $\Gamma$ sets. Additionally, the method includes detecting tumors in the prostate gland, and representing the biopsy cores as a capsule with a cylindrical volume having hemispherical end caps. The method includes setting a tumor detection area. The method includes generating the three-dimensional biopsy plan for significant tumors for a predefined number of biopsy cores and lengths. The method also includes generating the three-dimensional biopsy plan for insignificant tumors for a predefined number of biopsy cores and lengths. Additionally, the method includes defining a tumor detection area of a biopsy core as a capsule surrounding the biopsy core with a cylindrical volume having hemispherical end caps of the diameter of a tumor to be detected.

In accordance with still another aspect of the present invention, a system for calculating tumor detection probability of a biopsy plan includes a source of image data capable of reconstructing a target organ in three-dimensions. The system includes a non-transitory computer readable medium. The non-transitory computer readable medium is programmed for calculating significant and insignificant tumor detection probability from the image data. The program also includes generating a three-dimensional biopsy plan that increases the probability of the significant and insignificant tumor detection probability and calculating probability of a false negative detection of tumor using the three-dimensional biopsy plan to create a revised three-dimensional biopsy plan. The program further includes determining a number and length of biopsy cores required to execute the revised three-dimensional biopsy plan.

In accordance with yet another aspect of the present invention, the system further includes a computing device. The system includes calculating tumor detection probability with steps of setting a bounding box for a tumor detection area and a voxel size to discretize this volume at a predetermined level of resolution; iterating through all voxels; checking if a voxel center is within the tumor detection area, and if so add it to a set $\Gamma$; iterating through all voxels of set $\Gamma$; verifying if the voxel center falls within any of the biopsy cores of a set $\Pi$; counting the voxel with a center that falls within any of the biopsy cores of set $\Pi$ as sampled by adding it to a set $\Omega$; and calculating tumor prediction probability as the ratio of the number of elements of the $\Omega$ and $\Gamma$ sets. The system includes calculating tumor detection probability with steps of setting a volume of a tumor detection area and a voxel size to discretize the volume of the tumor detection area at a predetermined level of resolution to a set of voxels $\Gamma$; defining the tumor detection area of a biopsy core as a capsule surrounding the biopsy core with a cylindrical volume having hemispherical end caps of the diameter of the tumor to be detected; iterating through all voxels of $\Gamma$ and checking if a voxel center is within the tumor detection area of the biopsy cores of the plan; adding the voxel center to the sampled voxel set $\Omega$; and calculating tumor prediction probability as the ratio of the number of elements of the detected voxel set $\Omega$ and tumor search area voxel set $\Gamma$. The system includes detecting tumors in the prostate gland. The system includes detecting tumors in any organ with a boundary that is segmentable as a surface. The system includes representing the biopsy cores as a capsule with a cylindrical volume having hemispherical end caps. Further the system includes setting a tumor detection area. The system can also include a biopsy device.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 3A illustrates a schematic view of a definition of a capsule model.

FIG. 3B illustrates a schematic view of a modeled prostate with detected and undetected tumors.

FIG. 5A illustrates an image view of anatomical constraints for a transrectal biopsy.

FIG. 5B illustrates an image view of anatomical constraints for a transperineal biopsy.

FIG. 5C illustrates an image view of anatomical constraints for an angled biopsy.

FIG. 6A illustrates a schematic view of an initial biopsy plan for a transrectal biopsy.

FIG. 6B illustrates a schematic view of an initial biopsy plan for a transperineal biopsy.

FIG. 6C illustrates a schematic view of an initial biopsy plan for an angled biopsy.

FIG. 9 shows a transrectal 12-core, 18 mm core length biopsy of 40 cm$^3$ prostate. The systematic plan is shown on the left and the optimized plan is shown on the right with capsules (top) and cores (bottom). The optimization increases the probability of significant tumor detection ($^sP$) from 42.5% to 54.4%.

FIG. 12A illustrates a graphical view of a graphical view of $^sP$ versus core length for different prostate sizes.

FIG. 12B illustrates a graphical view of $^iP$ versus core length for different prostate sizes.

FIG. 12C illustrates a graphical view of $^sP/^iP$ versus core length for different prostate sizes.

DETAILED DESCRIPTION OF THE PREFERRED EMBODIMENTS

Figure 1C:
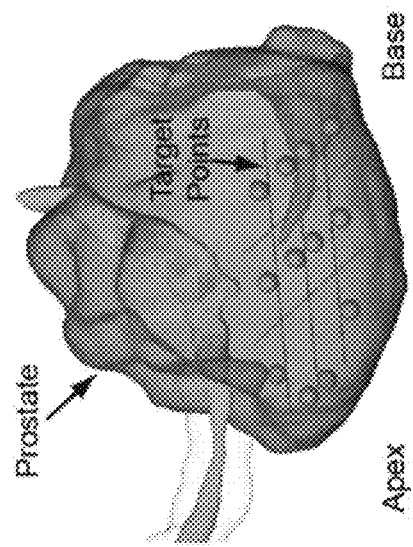
FIGS. 1A-1C illustrate schematic views of biopsy schemes in 2D and an example of its application in 3D.
Figure 1B:
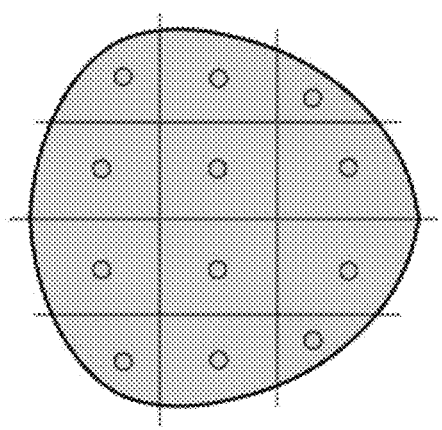
Figure 1A:
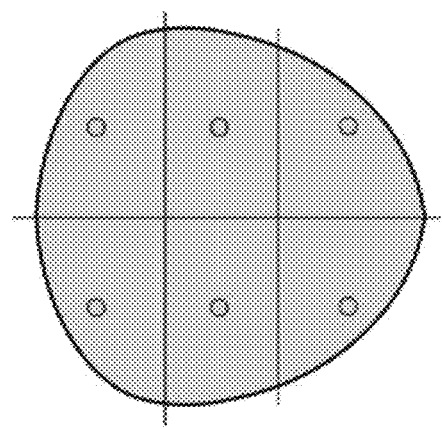

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method for calculating clinically significant tumor (determined by size) detection probability of a given biopsy plan and a method for generating a 3D biopsy plan that maximizes this tumor detection probability with a predefined number of biopsy cores and core length. A capsule (cylindrical with hemispherical ends) shaped volume that is coaxial and centered on the biopsy core is modeled to represent the volume that a biopsy core may sample. A tumor is considered detected if its center is within this capsule, assuming that tumors are spherical. For a single core biopsy, sampled volume is defined as the volume of the intersection between the respective capsule and the prostate. The probability of detecting a significant tumor, determined by its size, with this single core is the ratio of sampled volume to total prostate volume. For multiple core biopsy, the probability of detecting a significant tumor is defined as the ratio of the combined, non-overlapping volume of individual sampled volumes to total prostate volume.

An optimization method is used to generate a 3D biopsy plan that maximizes probability of tumor detection for predefined biopsy core numbers and length. The risk of detecting insignificant tumors, also determined by size, and the probability of a false negative result is also automatically calculated. The present invention also includes a method to determine the number and length of biopsy cores required for individual patients determined by the balance of the insignificant/significant probability of detection, prostate size and shape, based upon the previously explained 3D biopsy plan generation method.

The actual tissue volume extracted from a biopsy core is very small, on the order of 0.005 cm³ for a typical 18 Ga prostate biopsy needle. This represents only 0.02% of a 24 cm³ prostate. It would then follow that 4,800 needles would be required to fully sample the prostate. Fortunately, searching for clinically significant tumors requires substantially less cores.

Figure 2:
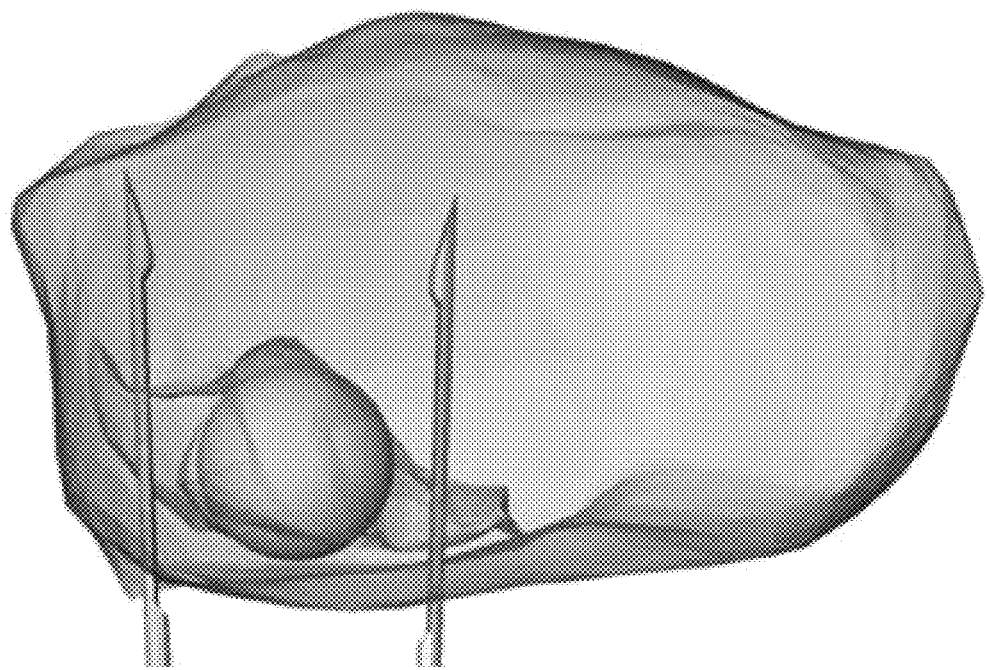
FIG. 2 illustrates a schematic view of a model prostate with a tumor and a representation of a spherical model tumor being undetected by biopsy cores.

To develop the tumor detection probability model, it is assumed that tumors are spherical in shape. Although many tumor foci are not spherical, this model is the worst-case scenario because the sphere has the lowest surface to volume ratio making it hardest to detect per unit volume. In other words, the furthest distance between any two points is smallest on the sphere than any other shape of the same volume, as exemplified in FIG. 2. Therefore optimizations based on the spherical model will result in the highest density of biopsy cores. The spherical model also offers the advantage of simplicity which enables the development of the capsule model presented in the next section.

Next, it is assumed that the probability of tumor occurrence is uniform throughout the prostate volume, although the majority of tumors occur in the peripheral zone of the prostate. This also represents a worst-case scenario, since only sampling certain regions of the prostate would require less biopsy cores. In addition, the probability of tumor occurrence in different zones of the prostate could be implemented by applying weight factors to the regions based on statistical data.

Finally, the threshold of clinically significant tumor size is defined as ≥0.5 cm³ (sphere radius 4.924 mm) and insignificant tumor size≤0.2 cm³ (radius 3.628 mm).

The optimization algorithm attempted to find as many as possible of the large tumors (≥0.5 cm³). Unavoidably, this process also resulted in the detection of small tumors (≤0.2 cm³), which are undesirable to be sampled. Tumors that fall in the midrange size (>0.2 cm³ & <0.5 cm³) were not searched for, but not considered detrimental if found.

A real tumor was considered sampled if the biopsy core intersected the tumor. In the model, a spherical tumor was sampled if the axis of core (needle) intersected the sphere. From the computational standpoint, however, it is more convenient to assess if the center of the sphere is located within a capsule (a cylindrical shape with rounded ends) that is centered on the core. These two approaches were equivalent in terms of the tumor being sampled or not, as shown in FIGS. 3A and 3B.

The capsule model is a cylindrical shape with hemispherical ends (FIG. 3A). The radius of the capsule is equal to the radius (R) of the spherical tumor, and the length (L) of the cylinder equals the length of the core (biopsy core magazine slot on the needle).

This model allowed us to quantify the prostate volume that a needle sampled. Prostate biopsy needles are usually slim (18 Ga), making it convenient to neglect their thickness. This also represents a worst case scenario since the modeled volume is less than the actual.

A spherical tumor is considered detected if, and only if, the distance from its center to the axis of the needle is smaller than its radius (d≤R), which makes the center fall within the capsule. Therefore, the volume searched for a spherical tumor of radius R by a single needle core is the volume of the capsule with the radius of the sphere and the length of the core. FIG. 3B illustrates in 3D a spherical tumor being detected or not detected by the capsule model.

Numerically, the volume of the capsule is, $$V_C^R = \pi R^2 L + \frac{4}{3}\pi R^3 \qquad \text{(Eq. 1)}$$

The volume searched by one core within the prostate is, $$V_{s,1}^R = V_P \cap V_C^R \qquad \text{(Eq. 2)}$$

For multiple cores, individual core volumes do not simply sum up because the cores may intersect each other. Therefore, $$V_{s,n}^R = V_p \cap (V_{c,1}^R \cup V_{c,2}^R \ldots \cup V_{c,n}^R) \quad \text{(Eq. 3)}$$

The probability of detecting a tumor of radius R with n cores is:

$$P_n^R = \frac{V_{s,n}^R}{V_p} = \frac{V_p \cap (V_{c,1}^R \cup V_{c,2}^R \ldots \cup V_{c,n}^R)}{V_p} \quad \text{(Eq. 4)}$$

Since the radii of the significant (0.5 cm³) and insignificant (0.2 cm³) tumors are 4.924 mm respectively 3.628 mm, the significant and insignificant probabilities of detection are:

$$^sP = P^{4.924} \text{ and } ^iP = P^{3.628} \quad \text{(Eq. 5)}$$

The P, either significant or insignificant, is a function of the position and orientation of the biopsy cores relative to the gland. Core orientation may be conveniently parameterized by the location of the entry point of the biopsy needle and the position of the core center. Therefore, a biopsy plan for n cores may be defined as a state matrix Π(n×6) as:

$$\prod = \begin{bmatrix} e_{11} & e_{12} & e_{13} & c_{11} & c_{12} & c_{13} \\ \vdots & \vdots & \vdots & \vdots & \vdots & \vdots \\ e_{n1} & e_{n2} & e_{n3} & c_{n1} & c_{n1} & c_{n3} \end{bmatrix} \quad \text{(Eq. 6)}$$

Where, $E_{ij}(e_{i1}, e_{i2}, e_{i3})$ and $C_{ij}(c_{i1}, c_{i2}, c_{i3})$ are the needle entry point respectively the core center positions of core i.

Then, the P can be calculated using the following algorithm:
  Set a bounding box for the prostate and a voxel size to discretize this volume at a desired level of resolution. For simplicity, the coordinate system is the same of the image, but could be differently chosen.
  Iterating through all voxels, check if the voxel center is within the prostate gland, and if so add it to a gland set Γ.
  Iterating through all voxels of set Γ, verify if the voxel center falls within any of the capsules of Π.
  If so, count the voxel as sampled by adding it to a set Ω.
  Calculate P as the ratio of the number of elements of the Ω and Γ sets.
Then, the P can be calculated using the following algorithm:

$$P_n^R = \frac{N(\Omega)}{N(\Gamma)} \quad \text{(Eq. 7)}$$

Figure 4:
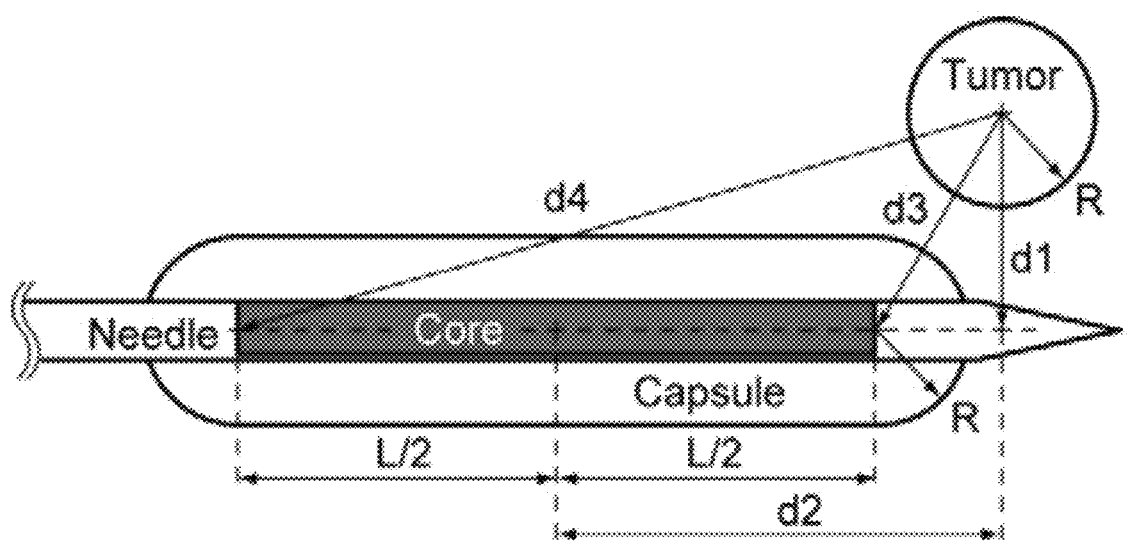
FIG. 4 illustrates a schematic view of detected and undetected tumor calculation based on the capsule model.

The algorithm above calculates a scalar P(Π) value for any given biopsy plan Π of n cores and tumor of radius R. The implementation included geometric evaluations that can be performed by classic methods available in public domain graphic toolkits. A fast way to check if a point is within the capsule FIG. 4, is to first calculate its distance d1 to the core axis. If d1>R, the point is excluded. If d1<=R, then the point is included if and only if one of the following relations holds: d2≤L/2 or d3≤R or d4≤R. Here, d2 is the projected distance from the point to the core center along the axis of the core, and d3, d4 are distances to the ends of the core, as shown in FIG. 4.

Core positions and entry points are subject to the following anatomical constraints:
1. Core positions should avoid the urethra (shown in FIGS. 5A-5C) to prevent hematuria and urinary retention.
2. The needle path must not interfere with the pubic arch bone.
3. The entry point constraints depend on the biopsy path. Their presence also reduces the rank of the state matrix defined by Eq. 6. Therefore, depending on the biopsy path, the parameterization of the plan may be simplified to a state matrix of independent variables Ψ. For the 3 biopsy plans:

For transrectal biopsy the needle is normally passed alongside the TRUS probe, which in turn is constrained at the anal sphincter, the pivot point of the probe. Thus, the entry points are constrained to move around the probe circumference (circle around the ultrasound probe in FIG. 5A). Accordingly, the entry points $E_{ij}$ are constrained to the probe circumference and determined by the probe rotation angle $θ_i$. Therefore, the state matrix Ψ (n×4) may be described as $$\psi = \begin{bmatrix} \theta_1 & c_{11} & c_{12} & c_{13} \\ \vdots & \vdots & \vdots & \vdots \\ \theta_n & c_{n1} & c_{n1} & c_{n3} \end{bmatrix} \quad \text{(Eq. 8)}$$

For template (grid) transperineal biopsy the direction of the needles are perpendicular to the template (parallel to each other). The entry points are constrained to the grid holes (FIG. 5B), discrete locations of the template $X_{ij}(x_{i1}, x_{i2})$. The core positions are restricted along the direction of the needle at depth $d_i$. Accordingly, the parameterized state matrix Ψ (n×3) may be described as:

$$\Psi = \begin{bmatrix} x_{11} & x_{12} & d_1 \\ \vdots & \vdots & \vdots \\ x_{n1} & x_{n1} & d_n \end{bmatrix} \quad \text{(Eq. 9)}$$

For angled transperineal biopsy, the entry points are constrained to the perineum (FIG. 5C) and may be parameterized to points $X_{ij}(x_{i1}, x_{i2})$ on a plane aligned with the perineum. Unlike the previous case, core center positions may be placed throughout the prostate. Accordingly, the state matrix Ψ (n×5) may be described as:

$$\Psi = \begin{bmatrix} x_{11} & x_{12} & c_{11} & c_{12} & c_{13} \\ \vdots & \vdots & \vdots & \vdots & \vdots \\ x_{n1} & x_{n2} & c_{n1} & c_{n1} & c_{n3} \end{bmatrix} \quad \text{(Eq. 10)}$$

In general, the state matrix Ψ is an (n×m) matrix, with m={4, 3, 5} for the transrectal, transperineal grid, and angled biopsies respectively.

The anatomical constraints were manually segmented from the pelvic anatomy of the Visible Human Project model to visualize the described constraints. In actual cases, these may be acquired from computer tomography (CT) or MRI of the pelvic region if required. In case of 3D TRUS imaging, the location of the sphincter could be approximated based on probe to image calibration. The required 3D geometric data of the prostate surface is also readily available when using novel biopsy devices such as position tracked probes and robots (Logiq-E9, GE Healthcare, Waukesha, Wis.). However, basic freehand 2D TRUS probes would not provide the data required by the method.

The optimization problem is to find the biopsy plan $\Psi$ that maximizes the probability of detection of significant tumors.

$$\text{Maximize } (^sP(\Psi)) \tag{Eq. 11}$$

Intuitively, the algorithm should search for a solution $\Psi$ that satisfies the constraints, fills the prostate as much as possible with capsules, avoids those extending out of the prostate, and minimizes their overlaps. The maximization may be implemented with iterative methods such as a gradient descent or pattern search optimization method.

Pattern search is a heuristic optimization algorithm that does not require the evaluation of the gradients of the objective function and was shown to work well on functions that are not continuous or differentiable. Compared to the classic gradient descent method that slides along the gradient to iteratively improve the solution, the pattern search uses a series of exploratory moves, one side and the other of each state variable, and retains the one that returns the best gain in the objective function.

The optimization starts with an initial biopsy plan $\Psi$. The state variables that determine the location of the entry points may be set zero. State variables that determine core locations may follow a sextant plan in the para-coronal plane for transrectal biopsy and transverse plane for transperineal biopsy (FIGS. 6A-6C).

At each step k, an exploratory move $\Delta^k$ is applied to each element $\psi_{ij}^{k-1}$ of the current state $\Psi^{k-1}$, where $$\Delta^k = [\delta_1, \delta_2, \ldots \delta_m], \text{ where } \delta_j > 0 \text{ for } j=1 \ldots m \tag{Eq. 12}$$

One by one, an exploratory move $\delta_j$ is applied to each side of each state matrix element while maintaining the other elements:

$$\psi_{ij\pm}^{expl} = \begin{cases} \psi_{qr}^{k-1} \pm \delta_j, & q = i \text{ and } r = j \\ \psi_{qr}^{k-1} & \text{otherwise} \end{cases} \tag{Eq. 13}$$

The probability of detection $^sP(\psi_{ij\pm}^{expl})$ calculated for all 2 nm exploratory moves. If any of these provides a positive gain relative to the previous state, the move $\Psi^{expl}$ that provided the maximum gain is retained to update the state matrix of the next iteration:

$$\psi^k = \begin{cases} \psi^{expl} \mid \text{Max}(^sP(\psi_{ij\pm}^{expl})) \text{ if } {}^sP(\psi_{ij\pm}^{expl}) - {}^sP(\psi^{k-1}) > 0 \\ \psi^{k-1} \text{ otherwise} \end{cases} \tag{Eq. 14}$$

If there is no positive gain, the exploratory move $\Delta$ is reduced to:

$$\Delta^k = \lambda \Delta^{k-1} \text{ with parameter } 0 < \lambda < 1 \tag{Eq. 15}$$

When this reaches a small value, it is then reset to the initial value $\Delta^0$ and the above steps are repeated to check convergence to a better optimal solution, until there is no improvement.

In the present case, an initial exploratory move was $$\Delta^0 = \begin{cases} 5.0 \text{ mm}, & (c_{ij}, x_{ij}, d_i) \\ 10 & (\theta_i) \end{cases},$$

the reduction parameter was $\lambda = 0.5$, and the exploratory move was considered small if the linear moves ($c_{ij}$, $x_{ij}$, $d_i$) were smaller than 0.1 mm (6 reductions).

Figure 7A:
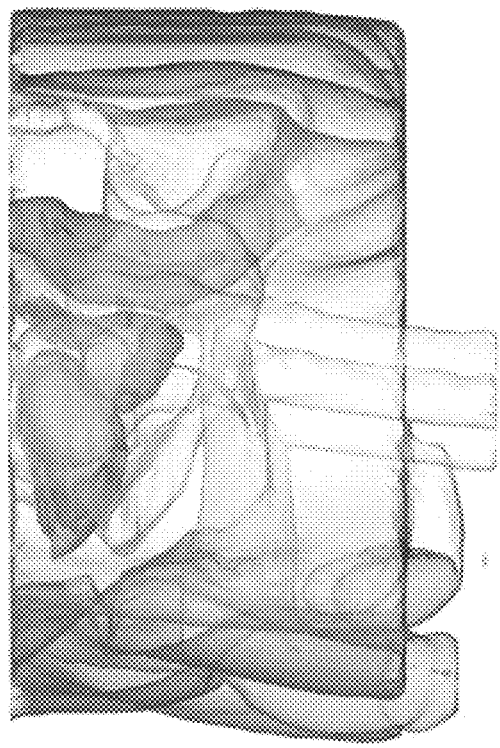
FIG. 7A illustrates a transverse view reconstructed VHP model.
Figure 7B:
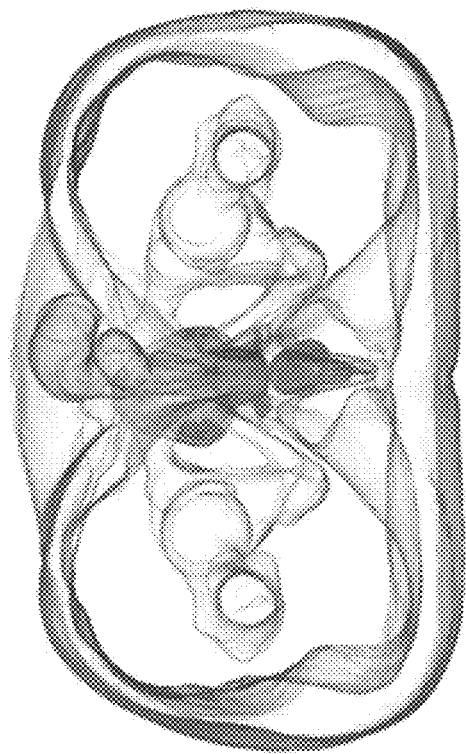
FIG. 7B illustrates a sagittal view of the reconstructed VHP model.

To simulate TRUS-biopsy and evaluate P, the male human anatomy was reconstructed from the Visible Human Project (VHP, National Library of Medicine). Manual segmentations of the prostate, bladder, urethra, rectum, and pubic bone with the perineal wall were done by an experienced urologist using the Amira Visualization platform (FEI Company, Burlington, Mass.) as in FIGS. 7A and 7B. The size of the prostate, 21.4 cm³, was also measured using the Amira Visualization platform. To simulate different prostate volumes, the VHP's prostate was uniformly scaled about the center of its bounding box to 5 sizes: 20 cm³, 40 cm³, 60 cm³, 80 cm³, and 100 cm³.

First, to determine convergence of the optimization method, the 12-core transrectal biopsy optimization using the typical 18 mm core length was performed for the 20 cm³ prostate. Optimization was started from 10 different initial states ($\Psi^0$). All these initial states were chosen as reasonable variants of the typical 12-core extended sextant biopsy plan (FIG. 1C), with variation in the position and orientation of the biopsy plane.

Then, the relationship between the number of cores and the size of the prostate was investigated, while maintaining the standard 18 mm core length. For this, the $^sP$ were evaluated for 18 biopsy plans of 6 to 40 cores (with increment of 2, added symmetrically on the left and right lobes) for each of the 5 prostate sizes (20 cm³ to 100 cm³, 20 cm³ increment).

Next, the relationship between the core lengths and the size of the prostate was investigated for the 12-core biopsy. For this, the $^sP$ were evaluated for 14 core lengths between 14 mm and 40 mm (2 mm increment) for each of the 5 prostate sizes.

Figure 8A:
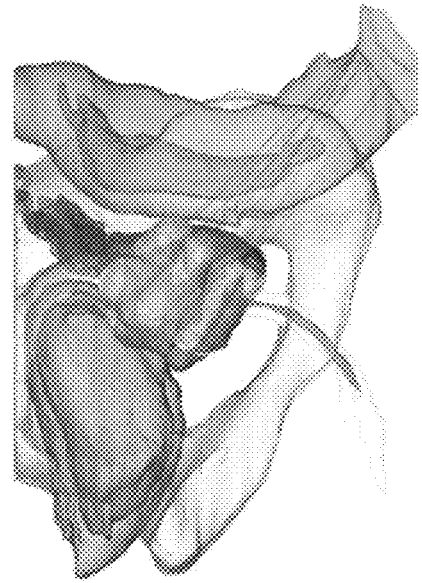
FIG. 8A illustrates a schematic view of a transrectal biopsy plan.
Figure 8B:
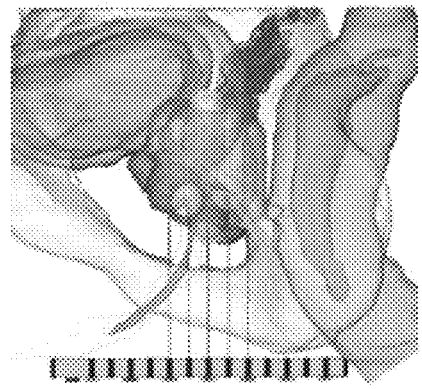
FIG. 8B illustrates a schematic view of a uniform grid biopsy plan.
Figure 8C:
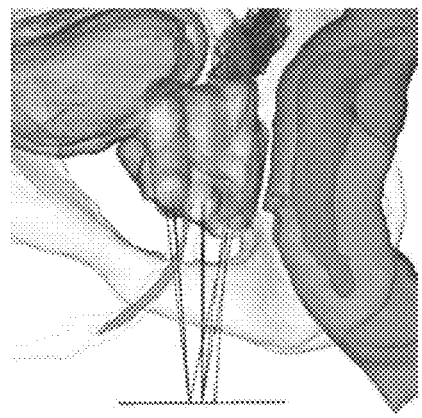
FIG. 8C illustrates a schematic view of an angled needle transperineal biopsy.

In all cases, the optimal biopsy plan $\Psi$ was determined by maximizing the significant tumor probability of detection Max ($^sP(\Psi)$) for all three biopsy paths (FIGS. 8A-8C). The probability of inadvertently detecting insignificant tumors with the optimal plan $^iP(\Psi)$ was then evaluated, as well as the ratios of the $^sP$ to $^iP$.

Figure 9:
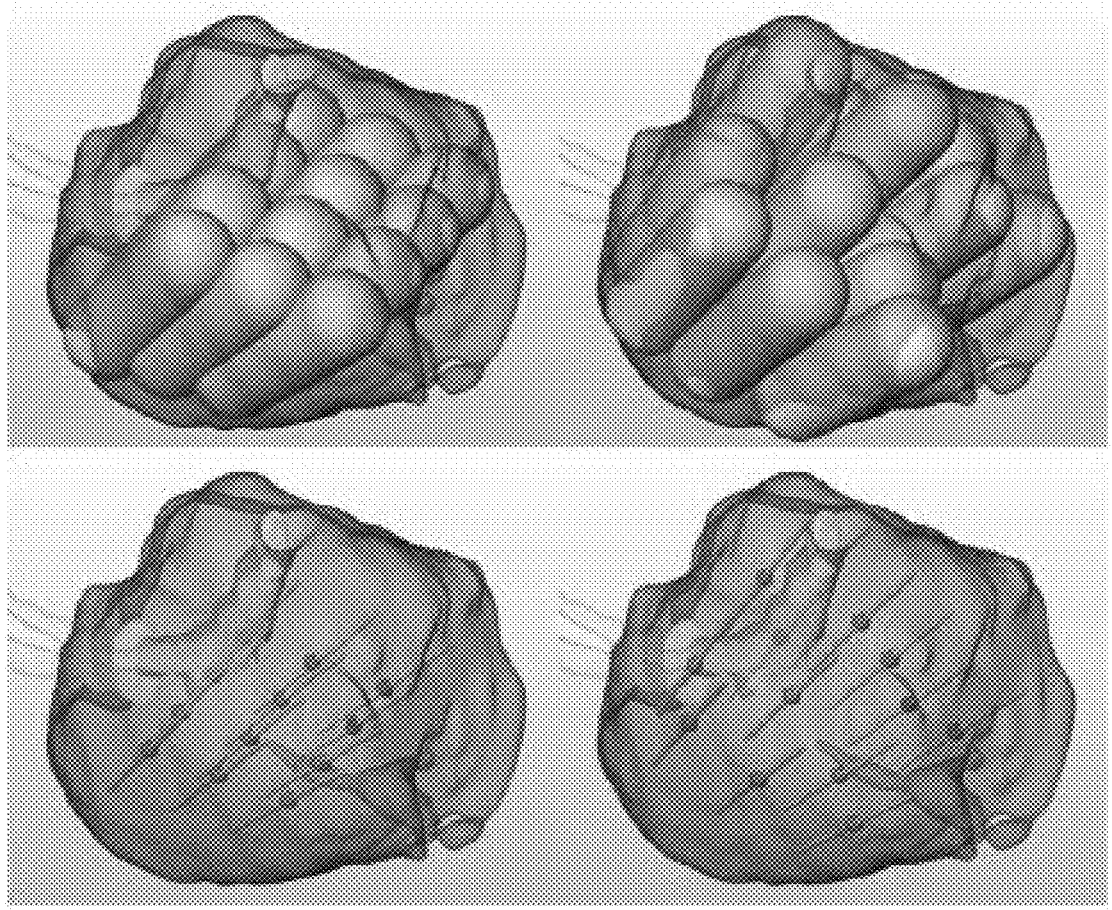
FIG. 9 illustrates schematic views of biopsy plans.

An example of a transrectal biopsy plan optimization that starts from the systematic biopsy plan is presented in FIG. 9 (for 12-cores, 18 mm core length, and 40 cm³ prostate size). The initial $^sP$ of the systematic biopsy plan was 42.5%. After optimization, the $^sP$ increased to 54.4%.

Figure 10:
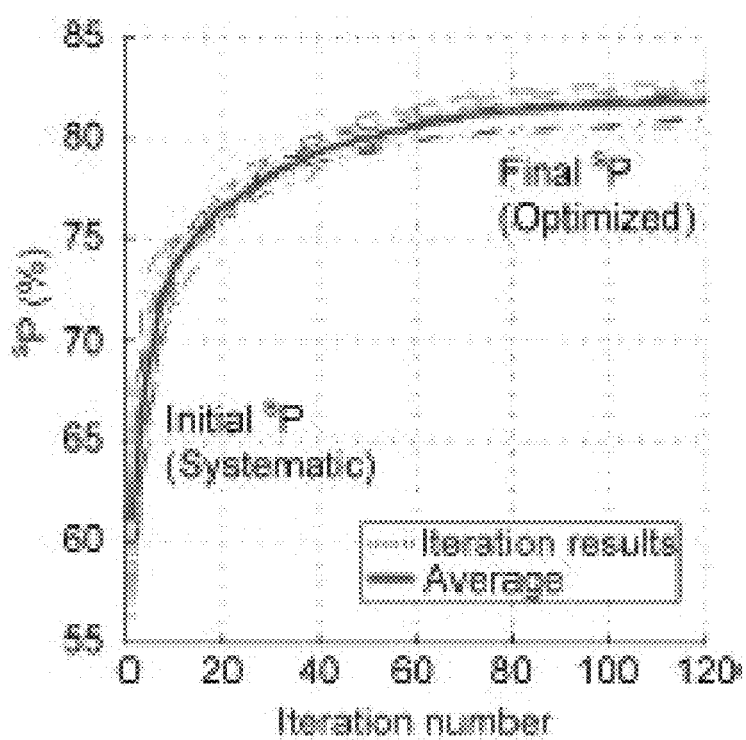
FIG. 10 illustrates a graphical view of iterative improvement in the probability of detection during the optimization process for an exemplary 20 cm$^3$ prostate size.

FIG. 10A shows the optimization result for 10 trials on a 20 cm³ prostate, each manually initialized with a slightly different systematic biopsy plane. The dotted lines denote the $^sP$ of 10 different trials, and the red solid line denotes the average of all trials. The optimized plan has a higher $^sP$ than the systematic biopsy plan. For a 20 cm³ prostate, the average $^sP$ of the initial systematic and the optimized biopsy plan are 61.1% and 81.8% respectively, with standard deviation of 3.6% and 0.7% respectively. The average computation time of each iteration and total computation was 0.29s(s) and 34.7(s) respectively using an Intel Core 17 CPU.

Figures 11A, 11B, 11C:
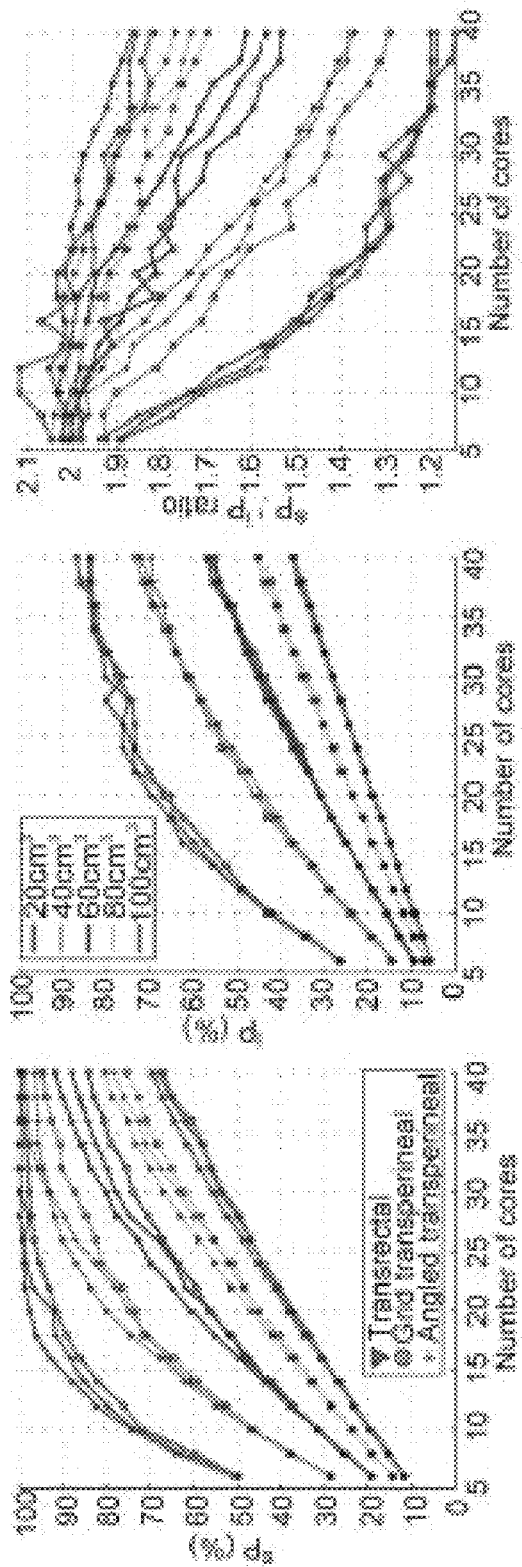
FIG. 11A illustrates a graphical view of $^sP$ versus the number of cores for different prostate sizes.
FIG. 11B illustrates a graphical view of $^iP$ versus the number of cores for different prostate sizes.
FIG. 11C illustrates a graphical view of $^sP/^iP$ versus the number of cores for different prostate sizes.

The results correlating the dependency of the $^sP$, $^iP$, and their ratio to the size of the prostate for a constant 18 mm biopsy core length are represented in FIGS. 11A-11C. These FIGS. show that if more cores are sampled the P increases, and the number of cores required to achieve a certain $^sP$ level is higher for larger prostates. The $^sP$ and $^iP$ are similar for different biopsy paths, with slightly higher $^sP$ values for the transrectal, then the angled transperineal, then the template transperineal biopsy (FIG. 11A).

At the same time, when more cores were used the $^iP$ also increased as in FIG. 11B. The $^sP$ to $^iP$ ratio decreased with the number of cores for all 3 biopsy paths as in FIG. 11C. For a 12-core extended sextant transrectal biopsy (18 mm) on a 40 cm$^3$ prostate, the $^sP$ and $^iP$ were 54.1% and 28.0% respectively, and the $^sP$ to $^iP$ ratio was 1.9.

For prostate sizes larger than 60 cm$^3$, 99% $^sP$ couldn't be reached even with 40 cores. Before the $^sP$ curves reached the saturation point, these were approximately linear, so that the number of cores required to achieve the same $^sP$ level is proportional to the prostate volume.

FIGS. 12A-12C depicts the dependency of the probability of cancer detection on the length of the biopsy cores for the common 12-core extended biopsy. The $^sP$ increases with the length of the core, as illustrated in FIG. 12A. This saturates at a length that is close to the depth of the prostate in the direction of biopsy (90% @ 25 mm for a 20 cm$^3$ prostate). The increase in the core length is also followed by increased $^iP$ (FIG. 12B). Before saturation, $^sP$ and $^iP$ were approximately linear to the core length. The ratio of $^sP$ to $^iP$ decreased with the core length for all 3 biopsy paths (FIG. 12C).

A Capsule Model is presented to facilitate the evaluation of the probability of prostate cancer detection that a biopsy plan may yield. This model may be subsequently used to optimize the biopsy plan geometry by maximizing the likelihood of cancer detection with a given number of biopsy cores.

Traditional systematic biopsy methods use a uniform distribution of cores throughout the prostate gland. However, these lack a clear geometric definition leaving room for subjective interpretation. The biopsy plans presented herein are fully defined by coordinates of the cores and their direction. Together with the Capsule model, these plans enabled the quantification of cancer detection likelihood and optimization of the biopsy plan. For example, the probability of significant cancer detection with 12 cores in a 20 cm$^3$ prostate is 61.1% for the sextant plan and may be optimized to 81.8%, assuming that both of these plans are perfectly executed. In real practice, with conventional freehand TRUS biopsy, the probability of significant cancer detection of the sextant was found to average only 43%, due to manual execution errors and subjective planning. Together, these results suggest that the biopsy may be improved by almost 40% by using optimized planning and precise biopsy methods such as robot-assisted biopsy targeting.

Moreover, the numerical results reported herein represent worst-case scenarios, where the tumors would all be at the clinically significant size limit (0.5 cm$^3$). Since actual tumors would frequently be larger, the values that were reported are the lowest detection rates to be expected. For the example above, a wel executed optimal plan would yield at least 81.8% detection, but may be as high as 100% if tumors are larger. This is further supported by the spherical shaped tumor model that is also the worst case scenario in this respect. The results presented herein are intuitive and agree with previously reported results, which showed that more and longer biopsy cores are needed for larger prostates up to a saturation limit. The findings are also in agreement with a recent study, which showed that increasing the core length and number in the anterior regions of the prostate improved the detection rate for clinically significant cancer.

Several groups have also reported quantitative cancer detection rates and proposed optimization methods. A recent study reported that the sextant 12-core biopsy plan with 2-4 additional anteriorly directed cores, all taken with a 22 mm core length, may yield 100% detection rate of the significant tumors in prostates≤50 cm$^3$. The results are in agreement since their tumor sizes ranged from 0.5 cm$^3$ to 5.0 cm$^3$, as discussed above.

With the shared experience of the prior studies, the model could be further updated to predict not only the lowest but also the expected detection rate, by using whole mounted prostate models in addition to the Visible Human Project model currently used.

On the other hand, other studies reported that 100% detection may not be achievable even with numerous cores, in other words that even the saturation biopsy may not saturate. Unfortunately, the results also agree with this finding. For example, if a 60 cm$^3$ prostate would have only one 0.5 cm$^3$ tumor, there would be at least 10% chance of missing it even with a perfectly executed biopsy of 40 cores (FIG. 11a).

The capsule model also enables the estimation of the risk of over diagnosing prostate cancer at biopsy, that is the risk of detecting insignificant cancer (<0.2 cm$^3$). The present invention provides for the probability of detecting insignificant cancer.

Results shows that the risk of detecting insignificant cancer ($^iP$) is a tradeoff of sampling more biopsy cores with the purpose of detecting significant cancer ($^sP$). Moreover, $^iP$ increases faster than $^sP$ with the number of cores, and especially for many cores and/or smaller prostates. Thus, careful consideration for overdetection should be given when increasing the number of cores, according to graphs presented (FIGS. 11A-11C).

Herein the methods are applied to a Visible Human Project model. The methods could be applied to biopsy optimization in individual patients, provided that 3D imaging is available. A proper balance of the insignificant/significant probability of detection could be made in concordance with the number of cores required for the patient. The ultimate goal would be to determine the biopsy plan that would detect all significant tumors utilizing the lowest number of biopsy cores, and thus minimizing the probability of insignificant tumor detection as well as invasiveness. Moreover, even if the biopsy result is negative for prostate cancer, the biopsy plan would numerically give the likelihood of a false-negative result occurring, and thus help the management of disease.

In this example the analysis and results focused on decoupling the effect of the number of cores and the core length on the probability of cancer detection. However, performing the study exhaustively for all 3 biopsy paths, 5 prostate sizes, 18 core number sets, and 14 core lengths is feasible and has actually been performed. However, displaying these massive data in a comprehensive manner was challenging. Therefore, for the purpose of this application only selected data that is relevant to the methods and from a clinical standpoint is presented.

In addition to traditional sextant methods, several studies have used 3D biopsy planning and considered the direction of the cores not only their core center position. In this example, the directionality of the core planning was improved by using realistic anatomical locations for needle access. Consideration of the limited access to the prostate caused by the constraints of the human anatomy makes the plans more realistic and practically applicable, including the depth of the cores.

Integrating the site of needle access with planning, as presented, sets imaging requirements that are both limiting and enabling. Imaging capable of reconstructing the prostate in 3D are required, such as tracked TRUS, CT, or MRI. In this respect, the methods presented apply directly to modern biopsy devices such as mechanically and magnetically tracked (Logiq-E9, GE Healthcare, Waukesha, Wis.) TRUS probes, image fusion systems (KOELIS, La Tronche, FRANCE) TRUS robots, as well as MRI-Safe robots. In turn, the use of these novel biopsy devices would substantially improve upon the accuracy of executing the proposed optimized biopsy plans.

The analytical model is based on several idealized assumptions. First, tumors are considered to be spherical shape rather than irregular, curvilinear, or fusiform. While this does not reduce the validity of the optimization, it does limit the use of the proposed methods in predicting the size of detected tumors. However, the size may be predicted by other methods that consider the length of the cancerous part of the biopsy core.

Second, the model assumes that tumors are evenly distributed within the gland while it is reported that approximately 68% originate from the peripheral zone (PZ) and 32% from the central gland (CG). This assumption may explain that $^sP$ are similar for the transrectal, and transperineal biopsy paths in the present invention, and that the required number of cores is directly correlated to the prostate size.

Both limitations may be overcome with further research, by correlating statistical information of tumor shape and zonal distribution from whole mount prostates. This additional information would further improve the algorithm to apply higher weight factors in high risk zones and accordingly distribute more cores in these regions.

The Capsule Model allows 3D geometric optimization of biopsy core positions and orientations based on 3D prostate imaging. As with all systematic biopsy methods, evenly distributing the cores increases the probability of cancer detection by preventing the cores being clustered or missing regions. While traditional sextant biopsy plans lack the geometric blueprint of the plan, the proposed plans are defined by coordinates, optimized in a geometric sense, and consider anatomic constraints of the biopsy path, either transrectal or transperineal approach. Results showed that more and longer cores are required for higher probability of detection and in larger glands. However, these also increase the biopsy-associated morbidities and detection of insignificant cancer which may contribute to PCa overdetection. The results may be used to balance the number of biopsy cores based on significant/insignificant detection expectancy, in addition to other clinical considerations. The present invention is the first to quantitatively estimate the insignificant portion.

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method of biopsy planning comprising:
    calculating significant and insignificant tumor detection probability, wherein significance is based on tumor size;
    generating a three-dimensional biopsy plan that increases the probability of the significant and insignificant tumor detection probability;
    calculating probability of a false negative detection of tumor using the three-dimensional biopsy plan to create a revised three-dimensional biopsy plan; and
    determining a number and length of biopsy cores required to execute the revised three-dimensional biopsy plan.

2. The method of claim 1 further comprising implementing the method using a non-transitory computer readable medium.

3. The method of claim 1 further comprising:
    setting a bounding box for a tumor detection area and a voxel size to discretize this volume at a predetermined level of resolution;
    iterating through all voxels;
    checking if a voxel center is within the tumor detection area, and if so add it to a set $\Gamma$;
    iterating through all voxels of set $\Gamma$;
    verifying if the voxel center falls within any of the biopsy cores of a set $\Pi$;
    counting the voxel with a center that falls within any of the biopsy cores of set $\Pi$ as sampled by adding it to a set $\Omega$; and
    calculating tumor prediction probability as the ratio of the number of elements of the $\Omega$ and $\Gamma$ sets.

4. The method of claim 1 further comprising:
    setting a volume of a tumor detection area and a voxel size to discretize the volume of the tumor detection area at a predetermined level of resolution to a set of voxels $\Gamma$;
    defining the tumor detection area of a biopsy core as a capsule surrounding the biopsy core with a cylindrical volume having hemispherical end caps of the diameter of the tumor to be detected;
    iterating through all voxels of $\Gamma$ and checking if a voxel center is within the tumor detection area of the biopsy cores of the plan;
    adding the voxel center to the sampled voxel set $\Omega$; and
    calculating tumor prediction probability as the ratio of the number of elements of the detected voxel set $\Omega$ and tumor search area voxel set $\Gamma$.

5. The method of claim 1 further comprising detecting tumors in the prostate gland.

6. The method of claim 1 further comprising detecting tumors in any organ with a boundary that is segmentable as a surface.

7. The method of claim 1 further comprising representing the biopsy cores as a capsule with a cylindrical volume having hemispherical end caps.

8. The method of claim 1 further comprising setting a tumor detection area.

9. The method of claim 1 further comprising generating the three-dimensional biopsy plan for significant tumors for a predefined number of biopsy cores and lengths.

10. The method of claim 1 further comprising generating the three-dimensional biopsy plan for insignificant tumors for a predefined number of biopsy cores and lengths.

11. The method of claim 1 further comprising defining a tumor detection area of a biopsy core as a capsule surrounding the biopsy core with a cylindrical volume having hemispherical end caps of the diameter of a tumor to be detected.

12. A system for biopsy planning comprising:
a source of image data capable of reconstructing a target organ in three-dimensions;
a non-transitory computer readable medium programmed for:
calculating significant and insignificant tumor detection probability from the image data, wherein significance is based on tumor size;
generating a three-dimensional biopsy plan that increases the probability of the significant and insignificant tumor detection probability;
calculating probability of a false negative detection of tumor using the three-dimensional biopsy plan to create a revised three-dimensional biopsy plan; and
determining a number and length of biopsy cores required to execute the revised three-dimensional biopsy plan.

13. The system of claim 12 further comprising a computing device.

14. The system of claim 12 further comprising:
setting a bounding box for a tumor detection area and a voxel size to discretize this volume at a predetermined level of resolution;
iterating through all voxels;
checking if a voxel center is within the tumor detection area, and if so add it to a set $\Gamma$;
iterating through all voxels of set $\Gamma$;
verifying if the voxel center falls within any of the biopsy cores of a set $\Pi$;
counting the voxel with a center that falls within any of the biopsy cores of set $\Pi$ as sampled by adding it to a set $\Omega$; and
calculating tumor prediction probability as the ratio of the number of elements of the $\Omega$ and $\Gamma$ sets.

15. The system of claim 12 further comprising:
setting a volume of a tumor detection area and a voxel size to discretize the volume of the tumor detection area at a predetermined level of resolution to a set of voxels $\Gamma$;
defining the tumor detection area of a biopsy core as a capsule surrounding the biopsy core with a cylindrical volume having hemispherical end caps of the diameter of the tumor to be detected;
iterating through all voxels of $\Gamma$ and checking if a voxel center is within the tumor detection area of the biopsy cores of the plan;
adding the voxel center to the sampled voxel set $\Omega$; and
calculating tumor prediction probability as the ratio of the number of elements of the detected voxel set $\Omega$ and tumor search area voxel set $\Gamma$.

16. The system of claim 12 further comprising detecting tumors in the prostate gland.

17. The system of claim 12 further comprising detecting tumors in any organ with a boundary that is segmentable as a surface.

18. The system of claim 12 further comprising representing the biopsy cores as a capsule with a cylindrical volume having hemispherical end caps.

19. The system of claim 12 further comprising setting a tumor detection area.

20. The system of claim 12 further comprising a biopsy device.

* * * * *